US012213501B2

(12) United States Patent
O'Hara et al.

(10) Patent No.: US 12,213,501 B2
(45) Date of Patent: Feb. 4, 2025

(54) METHODS FOR MODIFYING HIGH INTENSITY SWEETENER GLYCOSIDES

(71) Applicant: Optibiotix Limited, York (GB)

(72) Inventors: Stephen Patrick O'Hara, York (GB); Oswaldo Hernandez, York (GB); Sofia Kolida, York (GB)

(73) Assignee: Optibiotix Limited, York (GB)

( * ) Notice: Subject to any disclaimer, the term of this patent is extended or adjusted under 35 U.S.C. 154(b) by 852 days.

(21) Appl. No.: 17/044,870

(22) PCT Filed: Apr. 4, 2019

(86) PCT No.: PCT/GB2019/050993
§ 371 (c)(1),
(2) Date: Oct. 2, 2020

(87) PCT Pub. No.: WO2019/193356
PCT Pub. Date: Oct. 10, 2019

(65) Prior Publication Data
US 2021/0100272 A1 Apr. 8, 2021

(30) Foreign Application Priority Data
Apr. 4, 2018 (GB) .................................... 1805576

(51) Int. Cl.
A23L 27/30 (2016.01)
A23L 27/00 (2016.01)
A23L 33/125 (2016.01)
C12N 9/10 (2006.01)

(52) U.S. Cl.
CPC ............... *A23L 27/36* (2016.08); *A23L 27/86* (2016.08); *A23L 33/125* (2016.08); *C12N 9/1074* (2013.01); *C12Y 204/01019* (2013.01); *A23V 2002/00* (2013.01)

(58) Field of Classification Search
CPC ........ A23L 27/36; A23L 27/86; A23L 33/125; C12N 9/1074; A23V 2002/00
See application file for complete search history.

(56) References Cited

U.S. PATENT DOCUMENTS

| | | | |
|---|---|---|---|
| 2002/0065245 A1 | 5/2002 | Brouwers | |
| 2003/0236399 A1 | 12/2003 | Zheng et al. | |
| 2007/0082102 A1* | 4/2007 | Magomet | A23G 3/36 426/548 |
| 2010/0166679 A1* | 7/2010 | Abelyan | A23G 3/36 426/660 |
| 2010/0189861 A1* | 7/2010 | Abelyan | A23L 2/02 426/458 |
| 2010/0227034 A1* | 9/2010 | Purkayastha | A23G 9/32 426/302 |
| 2010/0255171 A1* | 10/2010 | Purkayastha | A23L 27/36 426/506 |
| 2011/0195169 A1* | 8/2011 | Markosyan | A23L 27/36 426/456 |
| 2012/0214751 A1* | 8/2012 | Markosyan | A61Q 11/00 514/23 |
| 2012/0214752 A1 | 8/2012 | Markosyan | |
| 2013/0287894 A1* | 10/2013 | Markosyan | A23L 2/60 536/18.1 |
| 2014/0030381 A1* | 1/2014 | Markysyan | A23L 2/60 426/48 |
| 2014/0227394 A1* | 8/2014 | Markosyan | A61K 36/28 426/583 |
| 2014/0227421 A1* | 8/2014 | Markosyan | A23L 27/33 426/583 |
| 2015/0030725 A1* | 1/2015 | Markosyan | A23L 27/30 426/52 |
| 2015/0157045 A1* | 6/2015 | Markosyan | A21D 13/062 426/48 |
| 2015/0164118 A1 | 6/2015 | Markosyan | |
| 2015/0305380 A1 | 10/2015 | Wu et al. | |
| 2017/0119032 A1* | 5/2017 | Patron | A23L 27/204 |
| 2017/0181443 A1 | 6/2017 | McCormick et al. | |
| 2017/0196247 A1* | 7/2017 | Markosyan | A23L 27/36 |
| 2017/0208847 A1 | 7/2017 | Markosyan | |
| 2017/0303565 A1 | 10/2017 | Markosyan et al. | |
| 2018/0020709 A1* | 1/2018 | Markosyan | A23L 27/36 426/7 |
| 2018/0044708 A1* | 2/2018 | te Poele | A23L 27/86 |
| 2018/0116266 A1* | 5/2018 | Jackson | A23L 27/36 |
| 2019/0071705 A1* | 3/2019 | Patron | A23L 2/60 |
| 2019/0297932 A1* | 10/2019 | Fletcher | C12P 19/56 |
| 2020/0054058 A1* | 2/2020 | Prakash | A23L 27/36 |
| 2020/0080120 A1* | 3/2020 | Zhang | A23L 2/60 |
| 2020/0093166 A1* | 3/2020 | Purkayastha | A21D 2/36 |

(Continued)

FOREIGN PATENT DOCUMENTS

JP H02131592 A 5/1990
JP H04288093 A 10/1992

(Continued)

OTHER PUBLICATIONS

English Translation for JP2003252895 published Sep. 10, 2003.*
Lim et al. Comprehensive Study on Transglycosylation of CGTase from Various Sources. 2021. Heliyon 7. pp. 1-16.*
Yu et al., "High Efficiency Transformation of stevioside into a single mono-glycosylated product using a cyclodextrin glucanotransferase from *Paenibacillus* sp. CGMCC 5316", "World J Microbiol Biotechnol", Sep. 22, 2015, pp. 1983-1991, No. 31, Publisher: Springer Science+Business Media Dordrecht.
Prakash, G.E. DuBois, J.F. Clos, K.L. Wilkens, L.E. Fosdick. (2008). Development of rebiana, a natural, non-caloric sweetener. Food and Chemical Toxicology. vol. 46, Issue 7, pp. S75-S82.
Caroline Hellfritsch, Anne Brockhoff, Frauke Stahler, Wolfgang Meyerhof, and Thomas Hofmann (2012). Human Psychometric and Taste Receptor Responses to Steviol Glycosides. Journal of Agricultural and Food Chemistry 2012 60 (27), 6782-6793.

*Primary Examiner* — Anthony J Weier
(74) *Attorney, Agent, or Firm* — Fredrikson & Byron, P.A.

(57) ABSTRACT

The present invention relates to high intensity sweetener glycosides which have been modified using a glycosyltransferase so as to reduce off-flavours. The invention also relates to uses of the modified high intensity sweetener glycosides and methods of production thereof.

5 Claims, 11 Drawing Sheets

(56) References Cited

U.S. PATENT DOCUMENTS

2021/0032669 A1* 2/2021 Philippe .................. C12P 5/007
2021/0095322 A1* 4/2021 Markosyan ............ A61K 47/26

FOREIGN PATENT DOCUMENTS

| | | | |
|---|---|---|---|
| JP | 2003252895 | A | 9/2003 |
| JP | 2009517032 | A | 4/2009 |
| KR | 20050097117 | A | 10/2005 |
| WO | 2013026151 | A1 | 2/2013 |
| WO | 2014150127 | A1 | 9/2014 |
| WO | 2017214026 | A1 | 12/2017 |
| WO | 2018112189 | A1 | 6/2018 |

* cited by examiner

METHODS FOR MODIFYING HIGH INTENSITY SWEETENER GLYCOSIDES

TECHNICAL FIELD OF THE INVENTION

The invention relates to high intensity sweetener glycosides which have been modified using a glycosyltransferase (such as a cyclodextrin glycosyltransferase (CGTase)) so as to reduce off-flavours. Such modified high intensity sweetener glycosides are particularly suited for use as low calorie sweeteners which can be used in combination with prebiotics.

BACKGROUND TO THE INVENTION

The global sweetener market is currently dominated by sugar and is forecast to reach $112 bn by 2022. There is an increasing move towards low calorie or calorie free sweeteners due to a number of health concerns associated with the excessive consumption of sucrose. A number of sweeteners, such as Mogroside V and steviol glycosides are classified as high intensity sweeteners (HIS) and have reported sweet potencies relative to sucrose of approximately 150×, 250× and 400× respectively. However, a number of HIS are associated with bitter or other "off" notes (such as liquorice flavours) which reduce their appeal to consumers.

It is an object of the present invention to address one or more of the problems associated with high intensity sweeteners. In particular, it is an object of the present invention to provide high intensity sweeteners which have reduced bitter or off notes. It would be desirable for high intensity sweeteners to be modified so as to reduce their bitter or off notes whilst substantially retaining their sweet potency. It would also be desirable for a method to be provided which can be used to modify high intensity sweeteners so as to reduce their bitter or off notes whilst substantially retaining their sweet potency.

SUMMARY OF THE INVENTION

In accordance with a first aspect of the present invention, there is provided high intensity sweetener glycoside which has been modified using a glycosyltransferase.

Preferably, the glycosyltransferase comprises cyclodextrin glycosyltransferase (CGTase, EC 2.4.1.19). CGTases are enzymes which catalyse coupling, cyclizing and hydrolysis of starch. The inventors have found that advantageously the use of CGTases can substantially reduce undesirable bitter and off-flavours in a number of high intensity sweetener glycosides whilst retaining similar sweetness profiles. The resultant oligosaccharides therefore demonstrate good flavour profiles and sweetness of between 140× and 223× that of sucrose at equivalent concentrations.

Preferably, the high intensity sweetener glycosides are selected from one or more (or a combination) of the following: Steviol glycosides (such as Rebaudioside A), Mogroside (such as Mogroside V), or derivatives thereof. The CGTase used will generally be specific for the high intensity sweetener glycosides being modified. For example, Stevia CGTase will be used to modify Steviol glycosides, whilst RebCGTase and MogCGTase will be used to modify Rebaudioside and Mogroside respectively.

If the high intensity sweetener glycosides being modified is Steviol glycosides, then preferably, up to 13 up to 12, or up to 11 glycosyl residues are left attached to the steviol aglycone. If the high intensity sweeter glycoside being modified is Mogroside V, then preferably, up to 20, up to 19 or up to 18 glycosyl residues are left attached to the aglycone. If the high intensity sweetener glycoside being modified is Rebaudioside A, then preferably, up to 15 up to 14, or up to 13 glycosyl residues are left attached to the steviol aglycone.

Preferably, the CGTase is derived from a bacterium. The bacterium may be selected from one or more of the following bacterium: *Paenibacillius, Thermoanaerobacter*, and *Geobacillius*. If the CGTase is derived from *Paenibacillus*, it is preferred that it is the *Paenibacillus macerans* species. Preferably, if the glycosides are Steviol glycosides then the CGTase is derived from a *Geobacillius* bacterium, or if the glycoside is Mogroside V then the CGTase is derived from a *Thermoanaerobacter* bacterium.

The glycosyl donor may comprise maltodextrin. Alternatively, the glycosyl donor may comprise gelatinized starch or soluble starch.

The modified high intensity sweetener glycosides will preferably have a reduced bitter and/or liquorice flavour when compared to an un-modified high intensity sweetener glycoside. Preferably, the flavour profiles of the modified high intensity sweetener will have the follow taste profiles:

Steviol Glycosides:
Bitter taste: reduction ratio/%=1.6/39%
Liquorice taste: reduction ratio/%=0/0%
Metallic: reduction ratio/%=2.7/63%
Mogroside V:
Bitter taste: reduction ratio/%=0
Liquorice taste: reduction ratio/%=1.7/41%
Metallic: reduction ratio/%=3/67%

In accordance with another aspect of the present invention, there is provided the use of the modified high intensity sweetener glycosides as herein above described, as a low or reduced calorie sweetener. It may also be used as a sucrose replacer, that is to say, it is used to remove and replace a portion of, or substantially all of, the sucrose in a product. The modified high intensity sweetener glycosides may also be incorporated in, or for incorporation, in or on, a foodstuff, a food supplement or a calorie restricted meal replacement product if desired.

The term "foodstuff" is intended to mean any material which can be safely ingested by a human or animal, including, but not limited to foods, beverages, cereals, bakery products, breaded and battered products, dairy products, confectionary, snacks, and meals. The term includes those products which require reconstitution prior to being cooked or eaten. The term also includes any food supplements or medicaments (such as vitamin tablets or antibiotic liquids).

It will be apparent to the skilled addressee that the modified high intensity sweetener glycosides may be incorporated into a product, by way of blending or mixing the glycosides with other ingredients. Alternatively, the modified high intensity sweetener glycosides may be used to coat a product.

In another aspect of the present invention, the modified high intensity sweetener glycosides may be used with or formulated in combination with a prebiotic.

The term "prebiotic" is intended to mean a selectively fermented ingredient that allows specific changes, both in the composition and/or activity in the gastrointestinal microflora that confers wellbeing and health benefits upon host.

Preferably the prebiotic comprises one or more (or a combination or one or more) selected from: inulin, fructooligosaccharides (FOS), galactooligosaccharides (GOS), α-gluco-oligosaccharides, β-glucans cellobiose, xylooligosaccharides and combinations thereof. More preferably, the prebiotic comprises fructans including fructo-oligosaccharides (FOS) and inulin and combinations of fructo-oligosaccharides and inulin.

The high intensity sweetener glycosides which have been modified using a glycosyltransferase (such as a cyclodextrin glycosyltransferase (CGTase)) may have been modified in the presence of the prebiotic.

In accordance with a yet further aspect of the present invention, there is provided a method for modifying high intensity sweetener glycosides so as to reduce one or more off-flavours, the method comprising:

a) contacting the high intensity sweetener glycosides with a glycosyltransferase under conditions effective to result in:

(i) at least a partial increase of glycoside chains of the high intensity sweetener glycosides; and/or (ii) at least a partial increase of the glycoside chains of a proportion of the high intensity sweeter glycosides;

so as to form modified high intensity sweetener glycosides or mixture of partially modified high intensity sweetener glycosides.

Preferably, the glycosyltransferase comprises a cyclodextrin glycosyltransferase (CGTase). In the method, using the preferred CGTase increases the glycosidic chains attached to the aglycone units.

In the method, the high intensity sweetener glycosides may be selected from one or more of the following: Steviol glycosides, Rebaudioside A, Mogroside V, or derivatives thereof.

In the method, the CGTase may be derived from one or more of the following bacterium: *Paenibacillus, Thermoanaerobacter*, and *Geobacillus*. If the glycosides are Steviol glycosides, then the CGTase may be derived from a *Geobacillus* bacterium. If the glycoside is Rebaudioside A, then the CGTase may be derived from a *Geobacillus* bacterium. If the glycoside is Mogroside V, then the CGTase may be derived from a *Thermoanaerobacter* bacterium.

The one or more off-flavours in the method may comprise one or more, or a combination of one or more, of the following flavours: bitter, liquorice or metallic.

Preferably, the high intensity sweetener glycosides are contacted with a cyclodextrin glycosyltransferase (CGTase) in the presence of maltodextrin.

It will be apparent to the skilled addressee that a number of the features of the composition listed in respect to a number of the aspects of the invention will be interchangeable with the composition administered in the present method.

DETAILED DESCRIPTION OF THE INVENTION

Embodiments of the present invention will now be described, by way of examples only.

Figure 3:
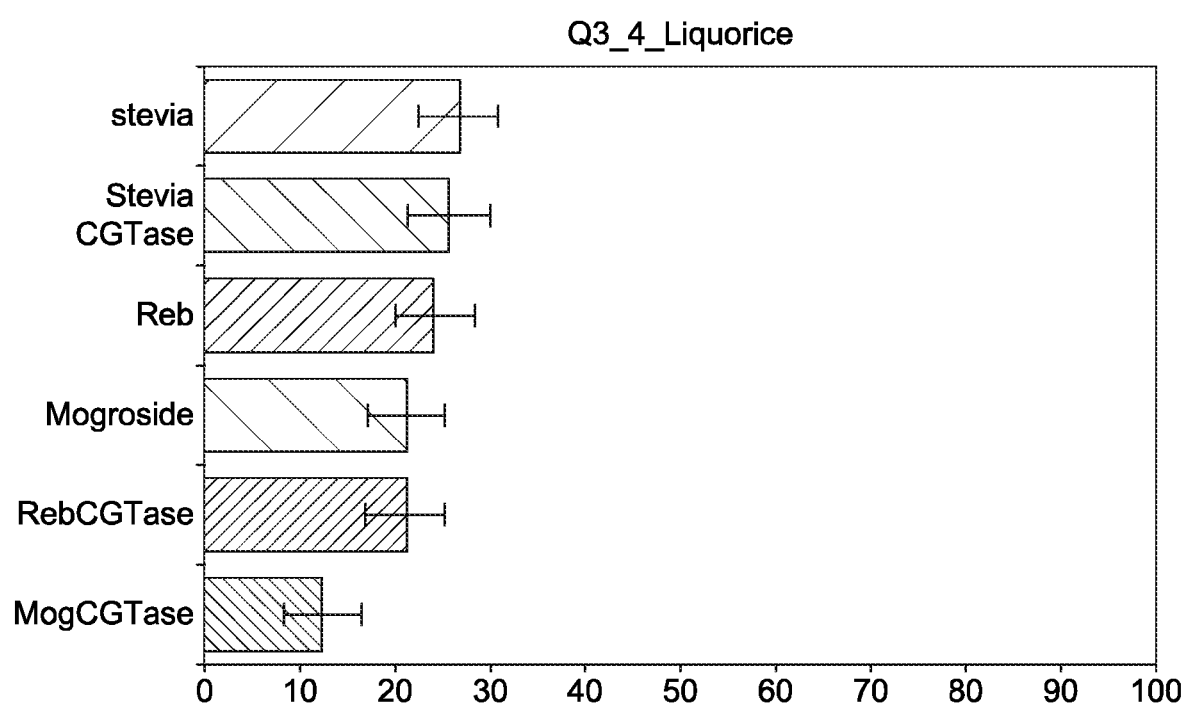
Figure 4A:
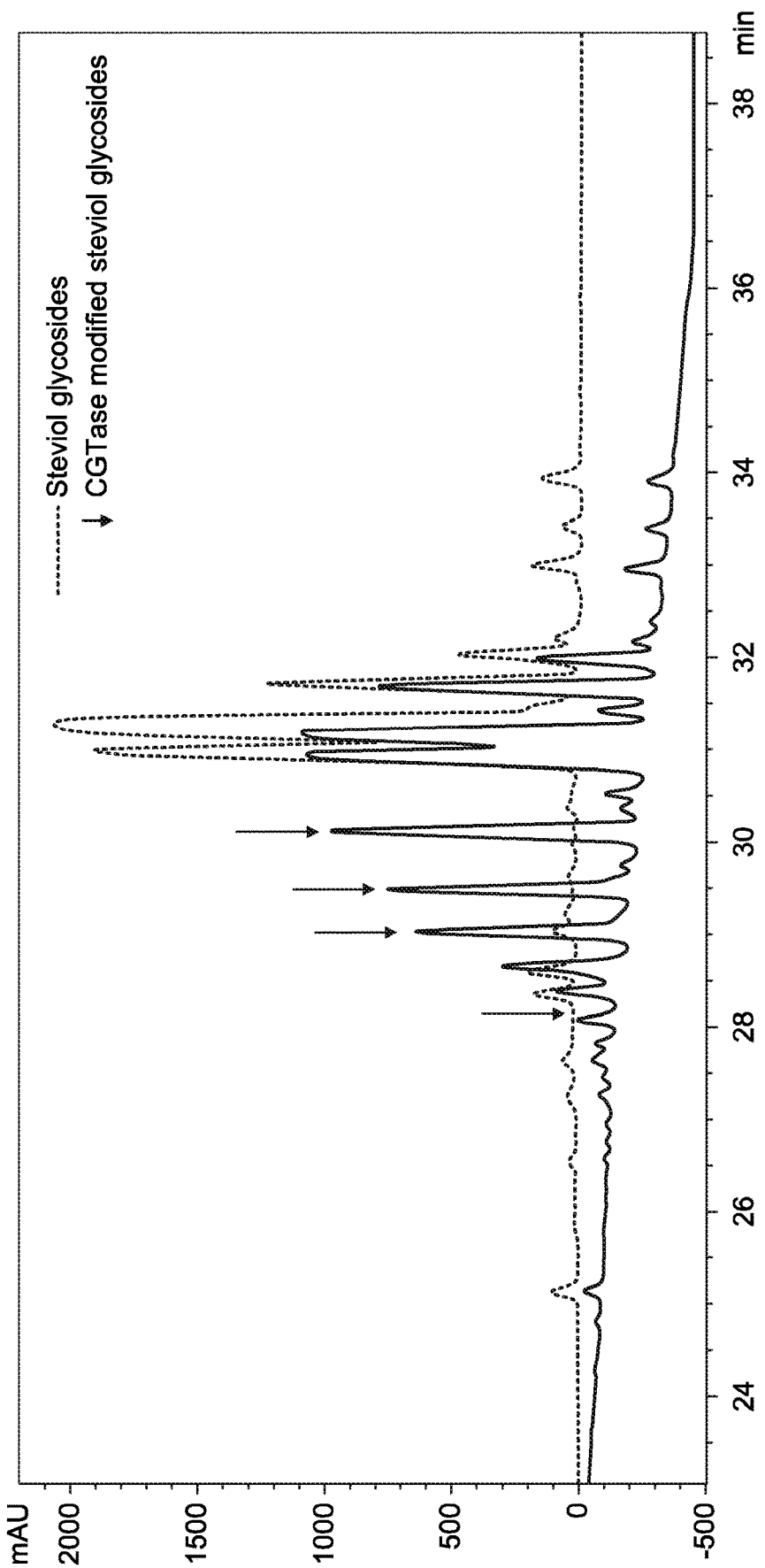
Figure 4B:
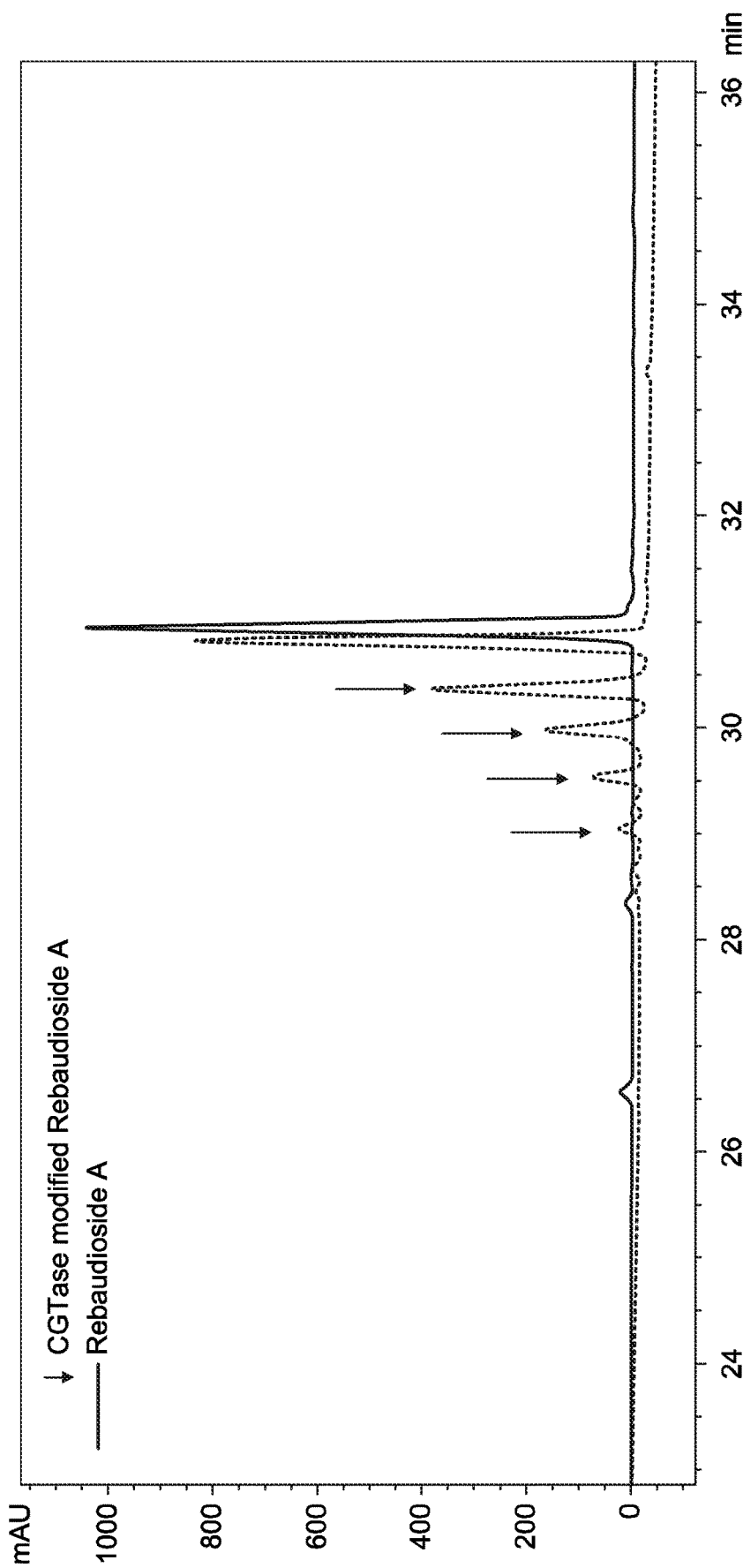
Figure 4C:
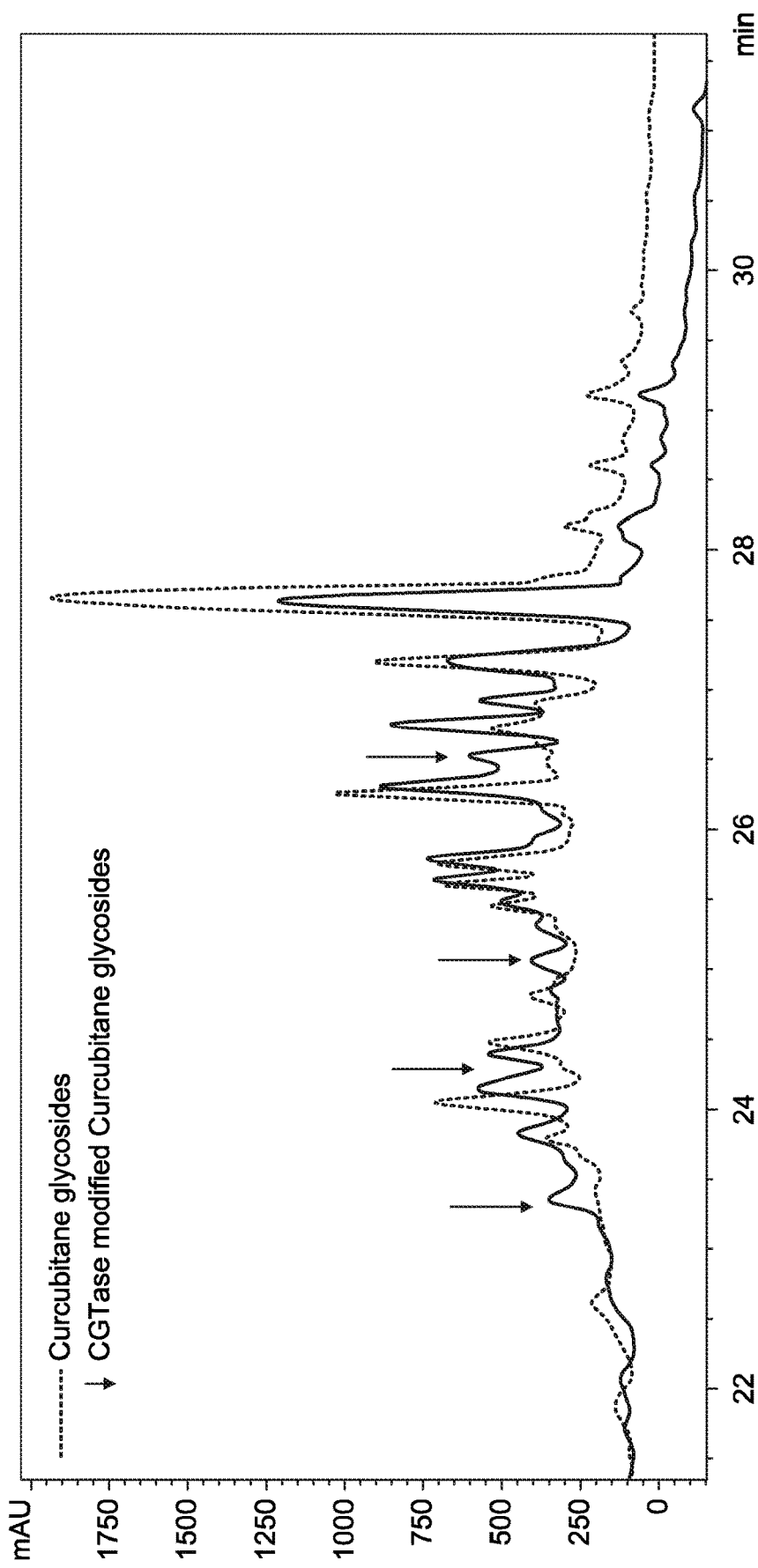
Figure 5A:
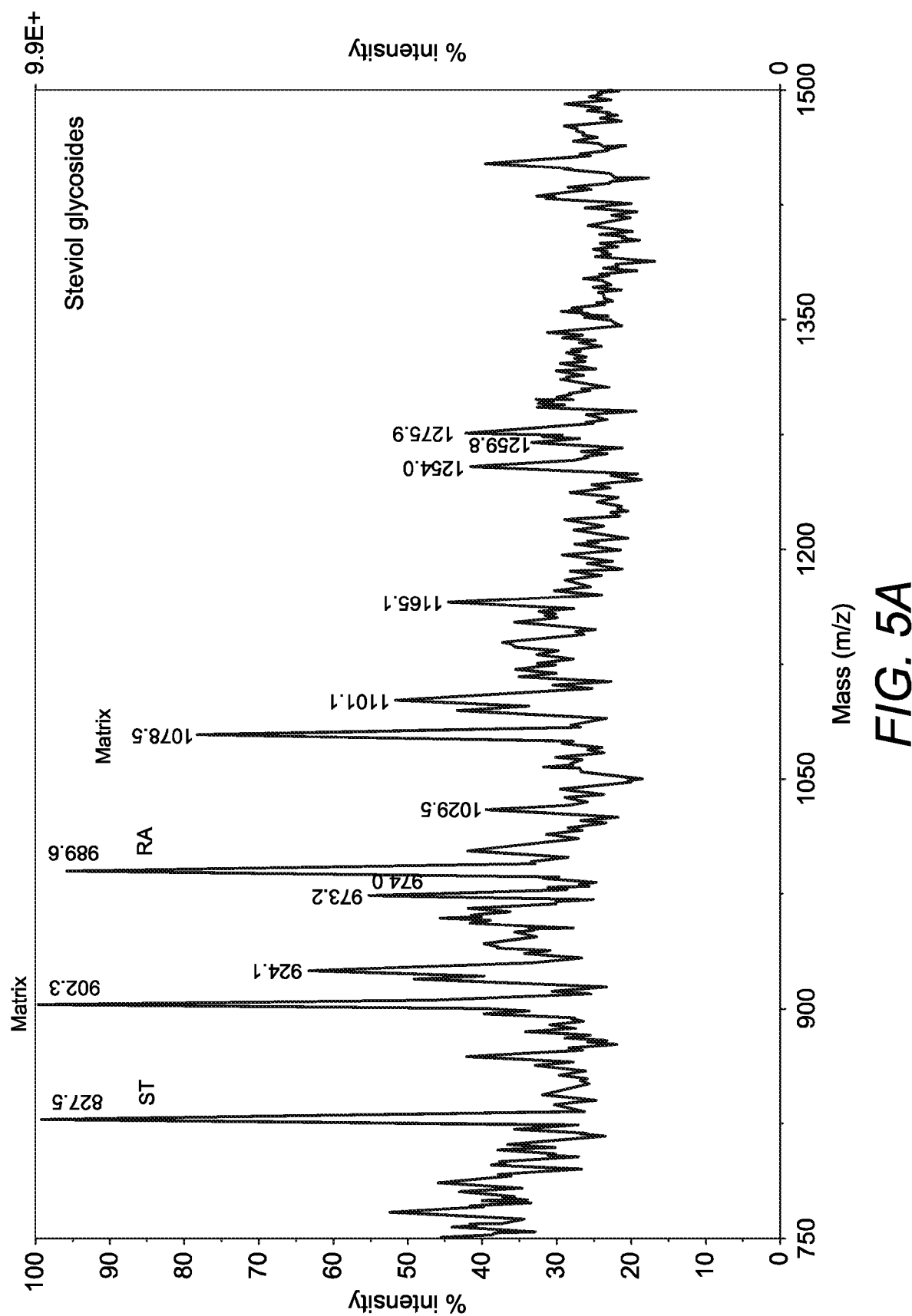
Figure 5A:
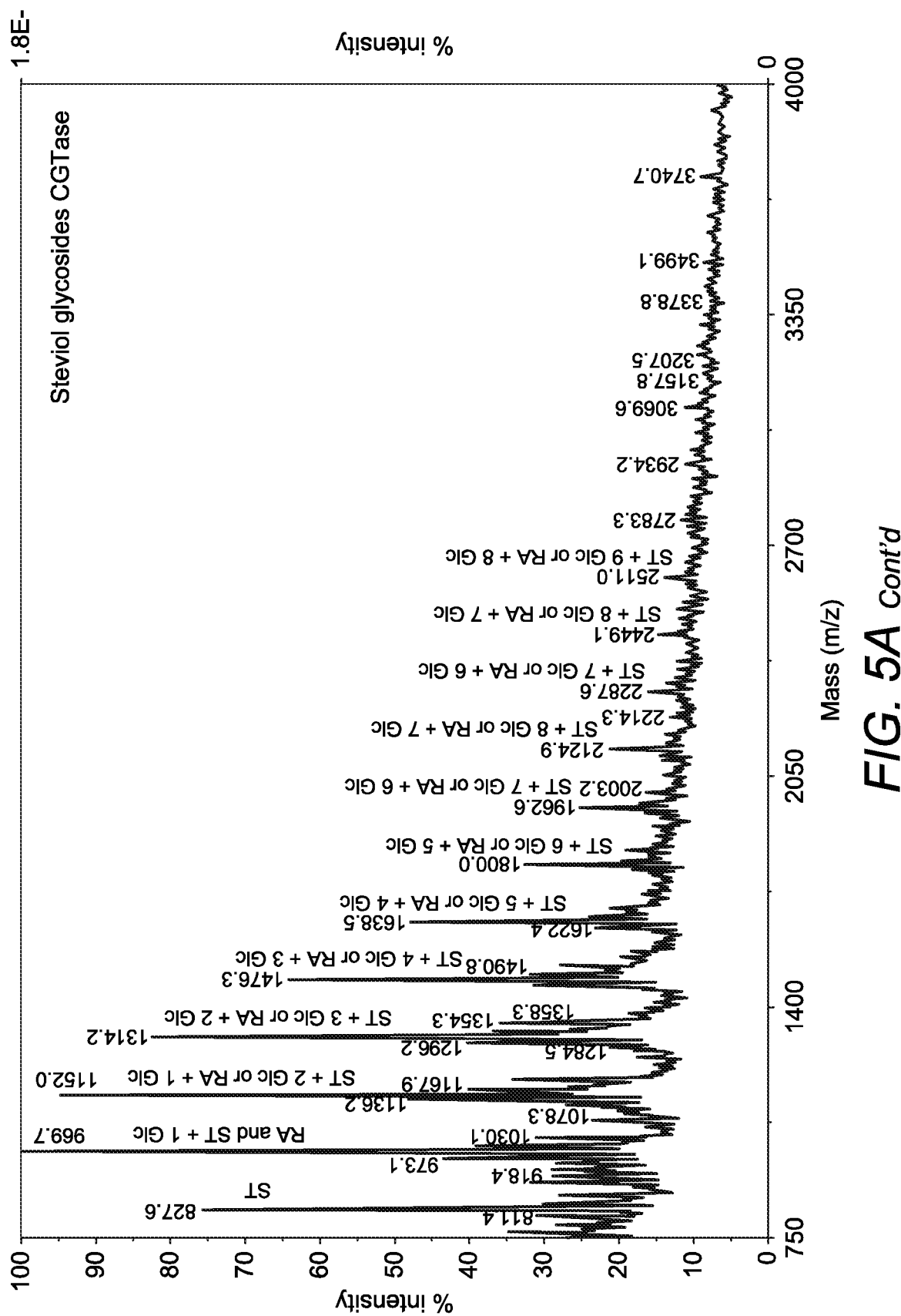
Figure 5B:
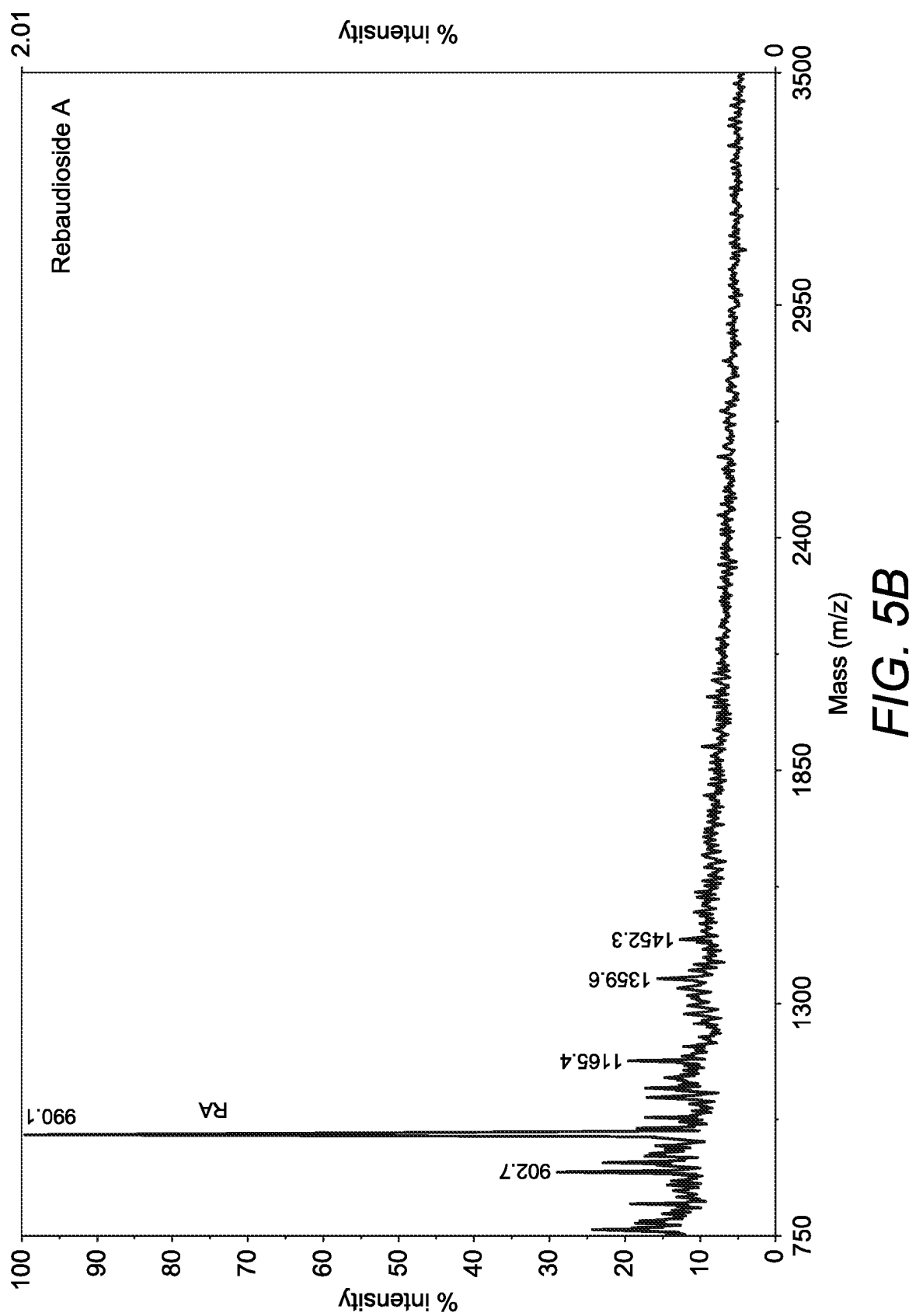
Figure 5B:
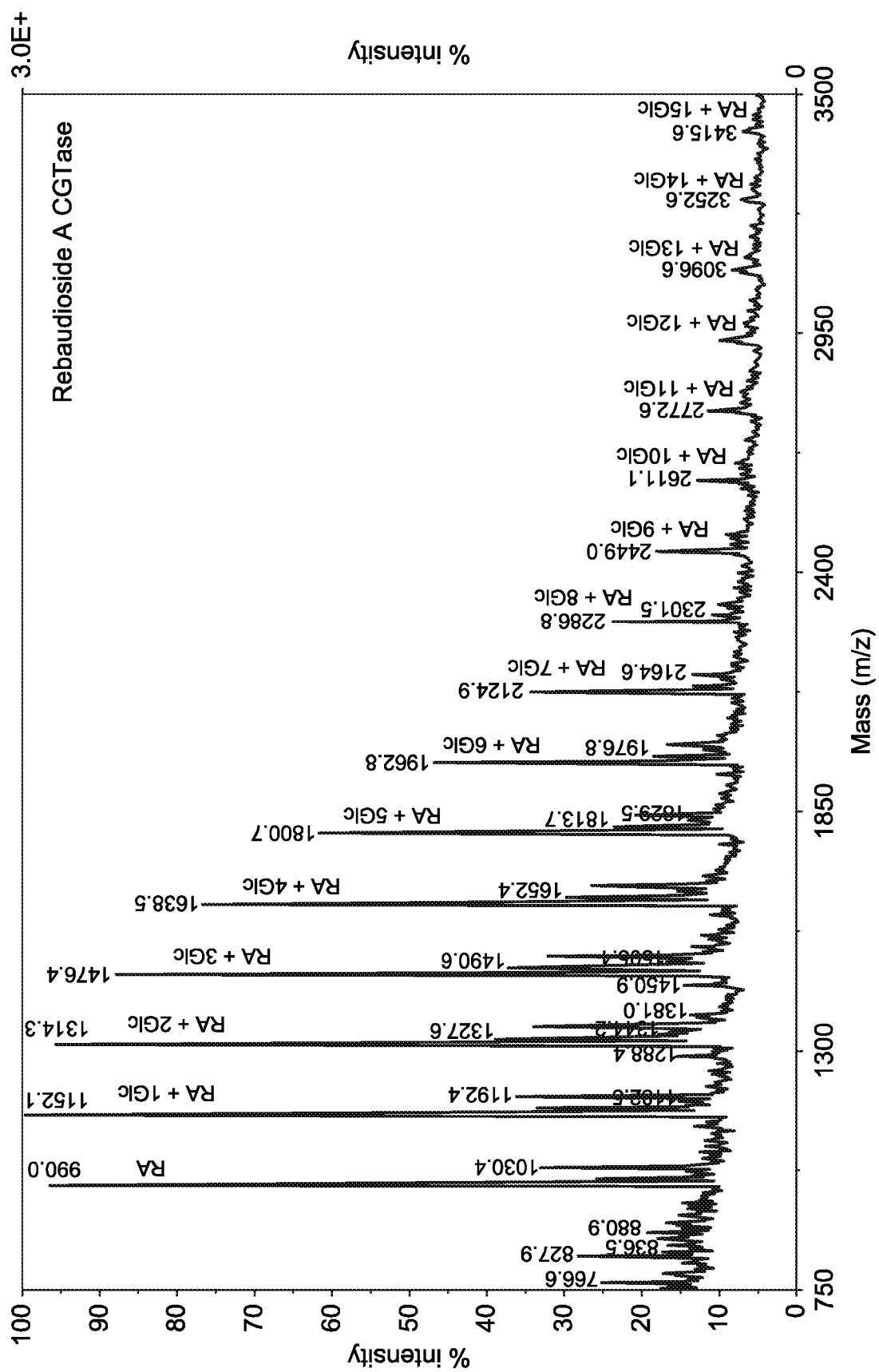
Figure 5C:
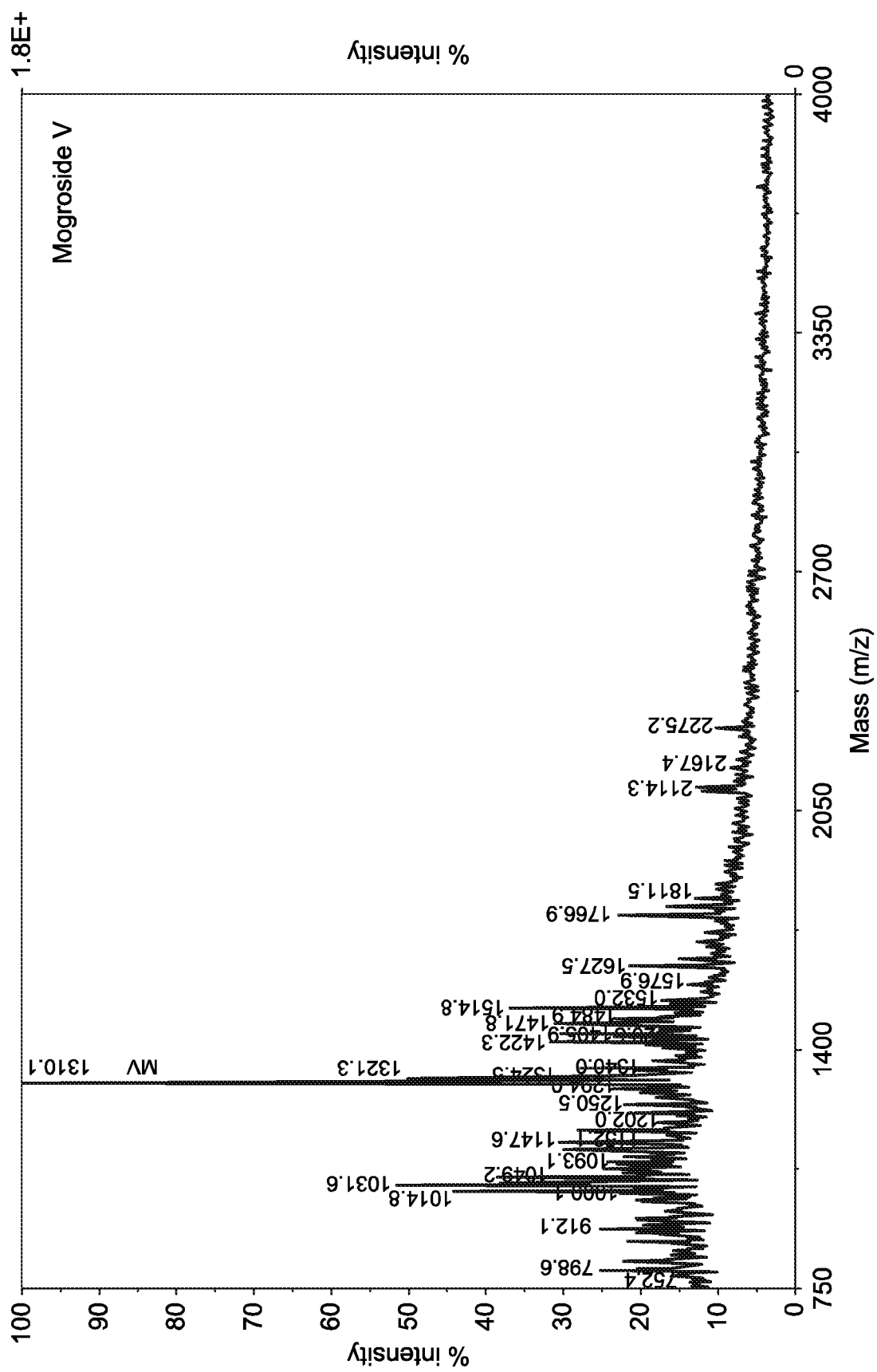
Figure 5C:
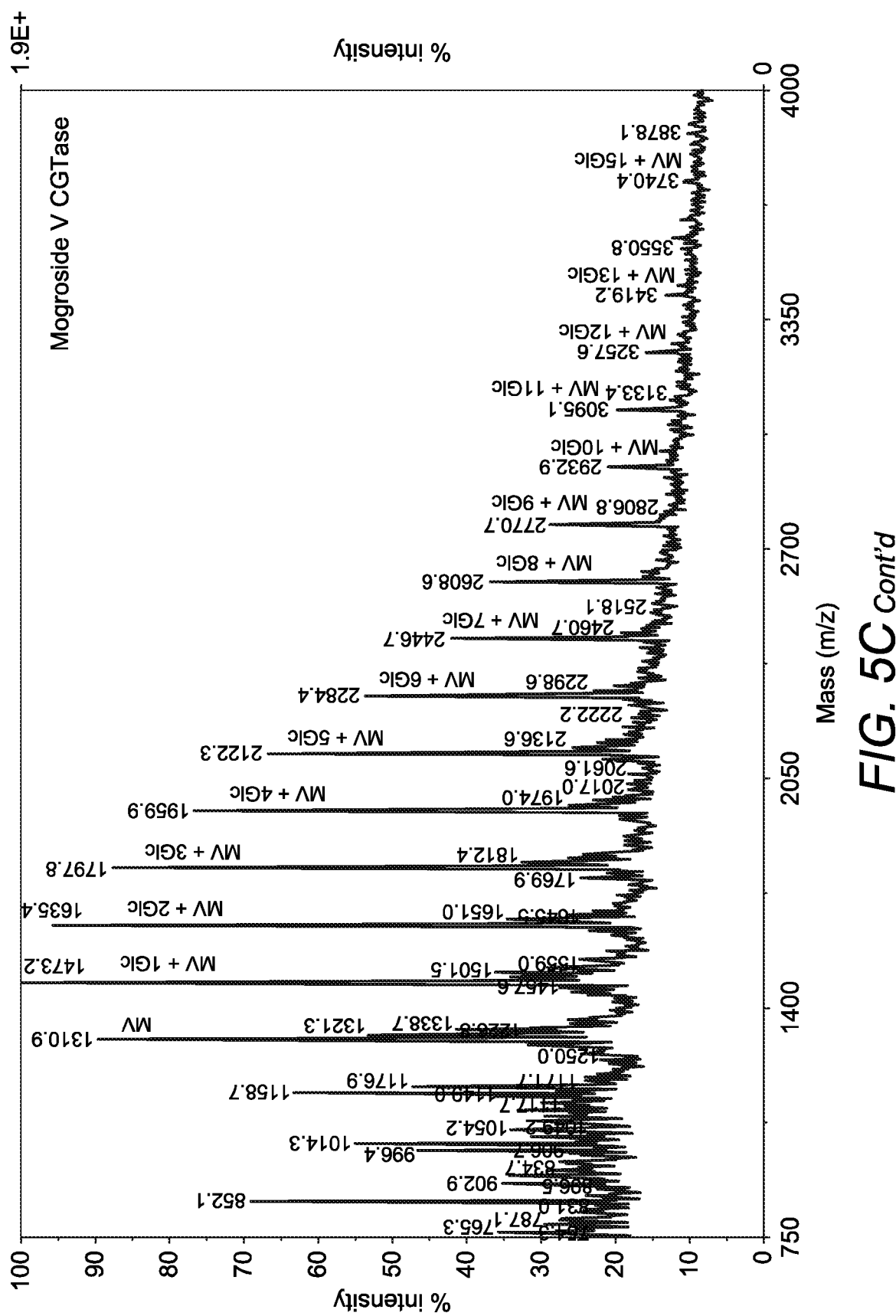

FIG. 3 is a bar chart showing the key attributes found to be significantly different between samples of Example 1 for a liquorice taste (bars represent mean values, error bars extend+/−half LSD); and FIGS. 4A, 4B, and 4C are graphs showing the different profiles for each target sweetener (A. steviol glycosides; B. rebaudioside A; and C. Mogroside V) with the corresponding compound before and after the CGTase enzymatic synthesis; and FIGS. 5A, 5B, and 5C are mass spectra graphs obtained from MALDI-ToF (A. steviol glycosides; B. rebaudioside A; and C. Mogroside V) with the corresponding compound before and after the CGTase enzymatic synthesis.

EXAMPLE 1

Sensory Profiling of Oligosaccharides Manufactured from High Intensity Sweeteners The aim of these experiments were to determine whether enzymatically modified glycosides were as sweet as their glycoside counterparts and whether the enzymatic modification reduced undesirable off-tastes such as bitter and liquorice notes. The samples were manufactured from food grade maltodextrin and food grade Steviol Glycosides or Rebaudioside A or Mogroside V. These samples were produced using commercially available food grade Cyclodextrin glycosyl transferase (CGTase) enzymes.

Initial Screening

As mentioned earlier, Steviol glycosides, Rebaudioside A and Mogroside V are high intensity sweeteners (HIS) reported to have sweet potency relative to sucrose of approximately 150×, 250× and 400× respectively. Often sweeteners are compared to sucrose at 8% sucrose equivalent (Prakash, G. E. DuBois, J. F. Clos, K. L. Wilkens, L. E. Fosdick. (2008). *Development of rebiana, a natural, non-caloric sweetener. Food and Chemical Toxicology*. Volume 46, Issue 7, Pages S75-S82. Previous literature (Caroline Hellfritsch, Anne Brockhoff, Frauke Stähler, Wolfgang Meyerhof, and Thomas Hofmann (2012). *Human Psychometric and Taste Receptor Responses to Steviol Glycosides. Journal of Agricultural and Food Chemistry* 2012 60 (27), 6782-6793) has shown bitterness of steviol glycosides to be most obvious at around 1000 µM which for Rebaudioside A would be 0.97 g/L, equivalent to 24% sucrose. However, solutions of 100 µM are also bitter which for Rebaudioside A would be 0.097 g/L, equivalent to 2.4% sucrose. Therefore, it was decided to test solutions at equivalent sweetness levels above 2% sucrose to ensure that both sweetness and bitterness could be evaluated in levels applicable to final application.

For the initial tasting sucrose standards were prepared at 4, 6, 8 and 10% (w/v) sucrose. Aiming for 8% sucrose equivalence all HIS and enzyme modified samples were also prepared at 0.32 g/L. From the initial tasting it had been concluded that the sucrose standard range needed to be reduced to 2, 4, 6 and 8% as the 10% sample was too extreme. The Rebaudioside A and Mogroside V, and their respective enzyme modified samples were considered sweeter than the Steviol glycosides and potentially too intense relative to the sucrose standards, therefore they were reduced in concentration to 0.24 g/L.

Preparation of Samples

The following commercial products were supplied by Optibiotix Health Ltd, York, UK to the Sensory Science Centre at the University of Reading, Department of Food and Nutritional Sciences: Rebaudioside A; Steviol glycosides; Mogroside V (50%); Rebaudioside A modified by CGTase; Steviol glycosides modified by CGTase; and Mogroside V (50%) modified by CGTase.

All samples underwent microbiological clearance testing and an volatile analysis to ensure less than 1000 ppm from the purification steps where ethanol was used.

All materials were stored at ambient temperature. Sucrose was purchased as white granulated sugar (Sainsburys Plc, London, UK). Water was Harrogate Spa mineral water (Harrogate Water Brands, Harrogate, UK).

Steviol glycosides and Steviol glycosides modified by CGTase (SteviaCGTase) were prepared at 0.32 g/L water. Rebaudioside A (RebA), Mogroside V and their respective enzyme modified equivalents (RebCGTase and MogCGTase) were prepared at 0.24 g/L water. Sucrose samples were prepared at 2.0, 4.0, 6.0 and 8.0% w/v. Weights were accurate to 3 decimal places, samples were made up in volumetric flasks. All samples dispersed well and solubilised easily in water.

TABLE 1

| Standard Number | Sucrose Concentration (% w/v) | Mean Rating (0-100) |
|---|---|---|
| 1 | 2.0 | 10 |
| 2 | 4.0 | 35 |
| 3 | 6.0 | 75 |
| 4 | 8.0 | 100 |

At the start of each scoring session the panel tasted the four reference samples in order of increasing strength to re-familiarise themselves with the positioning of these levels of sweetness on the line scale. The reference samples (10 mL) were served in transparent polystyrene cups (30 mL). They then palate cleansed with warm filtered tap water and low salt crackers (Carr's water crackers) before commencing the sample tasting session, and again between each sample scoring session.

Samples, labelled with random 3 digit codes, were presented in a balanced presentation order in a monadic sequential manner with a maximum of 6 samples per day. Samples were served at 23-24° C. (room temperature) with air conditioning of the room set to 23° C.

The panel used 16 attributes to define the oligosaccharide samples, as shown in Table 2 below.

TABLE 2

| | Stevia | Stevia CGTase | Reb | RebCGTase | Mogroside | MogCGTase | Fisher's LSD Value | Sample Significance (p) |
|---|---|---|---|---|---|---|---|---|
| Sweet Taste | $46.9^b$ | $47.1^b$ | $60.3^a$ | $49.6^b$ | $47.3^b$ | $35.6^c$ | 8.6 | 0.0001 |
| Overall Strength of Off Taste/Flavour | $39.9^a$ | $35.2^{ab}$ | $31.9^{bc}$ | $27.3^c$ | $25.6^{cd}$ | $19.2^d$ | 7.4 | <.0001 |
| Bitter Taste | $22.8^a$ | $13.9^b$ | $10.8^{bc}$ | $8.1^{bc}$ | $7.3^c$ | $5.4^c$ | 5.9 | <.0001 |
| Liquorice Flavour | $26.9^a$ | $25.8^a$ | $24.2^a$ | $21.3^a$ | $21.4^a$ | $12.6^b$ | 8.3 | 0.0168 |
| Sour Taste | $1.4^b$ | $4.4^a$ | $0.9^b$ | $2.9^{ab}$ | $1.2^b$ | $1.4^b$ | 2.6 | 0.0758 |
| Cooked sugar flavour | $2.7^{ab}$ | $1.8^b$ | $3.9^a$ | $2.6^{ab}$ | $3.2^{ab}$ | $1.4^b$ | 1.8 | 0.0875 |
| Cooling Sensation | $3.5^{ab}$ | $3.6^{ab}$ | $4.7^a$ | $3.1^{ab}$ | $2.6^{ab}$ | $2.4^b$ | 2.2 | 0.3143 |
| Cardboard/Stale Flavour | $0.8^{bc}$ | $3.7^a$ | $0.6^c$ | $2.8^{ab}$ | $0.7^c$ | $1.2^{bc}$ | 2.1 | 0.0197 |
| Metallic | $7.3^a$ | $2.7^{bc}$ | $2.7^{bc}$ | $2.2^{bc}$ | $3.4^b$ | $1.1^c$ | 1.8 | <.0001 |
| Salty Taste | $1.9^a$ | $2.2^a$ | $1.6^a$ | $2.3^a$ | $0.8^a$ | $1.5^a$ | 1.9 | 0.6422 |
| Crusty Bread Flavour | $0.3^c$ | $1.6^{abc}$ | $0.5^{bc}$ | $2.4^{abc}$ | $3.3^a$ | $3.2^{ab}$ | 2.7 | 0.1268 |
| Perfume Flavour | $0.0^a$ | $0.6^a$ | $0.4^a$ | $0.2^a$ | $0.3^a$ | $0.3^a$ | 0.6 | 0.6187 |
| Sweet Aftertaste | $24.8^{bc}$ | $27.8^b$ | $34.8^a$ | $25.6^{bc}$ | $28.2^b$ | $22.1^c$ | 5.8 | 0.0017 |
| Bitter Aftertaste | $14.7^a$ | $9.7^b$ | $6.5^{bc}$ | $7.0^{bc}$ | $4.6^c$ | $5.3^c$ | 4.1 | 0.0001 |
| Liquorice Aftereffect | $19.4^a$ | $14.3^{ab}$ | $11.6^{bc}$ | $9.9^{bc}$ | $10.8^{bc}$ | $7.3^c$ | 5.5 | 0.0016 |
| Cooling Aftereffect | $1.1^{ab}$ | $0.8^b$ | $2.1^a$ | $0.8^b$ | $1.6^{ab}$ | $1.2^{ab}$ | 1.2 | 0.2434 |

(Note: $^{abcdef}$superscripts of the same letter indicate no significant difference found at p 0.05)

Sensory Profiling Method

The trained sensory panel at the Reading Sensory Science Centre (UK) were employed for sensory profiling of the samples. There were 10 panellists with between 1 and 9 years' experience. A QDA (quantitative descriptive analysis) profiling approach was taken. The panel used the same vocabulary that they had developed as a consensus for the tasting sessions including the term Liquorice flavour which is characteristic note of steviol glycosides. The panel were retrained at the start of the sample set over 3 separate tasting sessions. This re-training focused on ensuring that they could reliably score sweetness relative to the new concentration of sucrose standard positions.

Rating was carried out independently using unstructured lines scales (scaled 0-100), in duplicate, in isolated sensory booths. However, in order to improve discrimination for sweetness, the four sucrose samples were used as standards and the mean values for each of these samples, as agreed by the panel, are shown in Table 1 below.

Panellists were given 5 mL of each sample to taste. The 5 mL was measured out by plastic syringe into the clear tasting cups (30 mL). The panellists ensured that they carefully sipped the sample and let it flow over the top of their tongue before swallowing. They sipped half of the sample into their mouth to score the first 6 attributes and the second half to score the following 6 attributes. Aftereffects were scored after a 30 second time delay.

Data Analysis

Data were analysed using a mixed model ANOVA where panellists were treated as random effects and samples as fixed effects, the main effects were tested against the sample by assessor interaction. Multiple pairwise comparisons were carried out using Fishers LSD and a significant difference was declared at an alpha risk of 5% (p≤0.05). Data analysis was carried out using Senpaq software (Qi Statistics, Reading, UK).

Sensory Profiling Results

Of the 16 attributes rated, 9 were significantly different between samples (as shown in Table 2 above).

Rebaudioside A (0.24 g/L) was significantly more sweet than Steviol gycosides (0.32 g/L) and Mogroside V (0.24 g/L). Enzyme modification reduced the sweetness of Rebaudioside A and Mogroside V, but not of steviol glycosides. Bitter taste was significantly higher for steviol glycosides than for Reb A or Mogroside V; however the enzymatic modification reduced the bitterness of the steviol glycosides. Steviol glycosides, Reb A and Mogroside V were all equivalent in liquorice flavour, although this was significantly reduced by enzymatic modification—but only of Mogroside V. All other taste and flavour attributes were rated at low levels.

Figure 1:
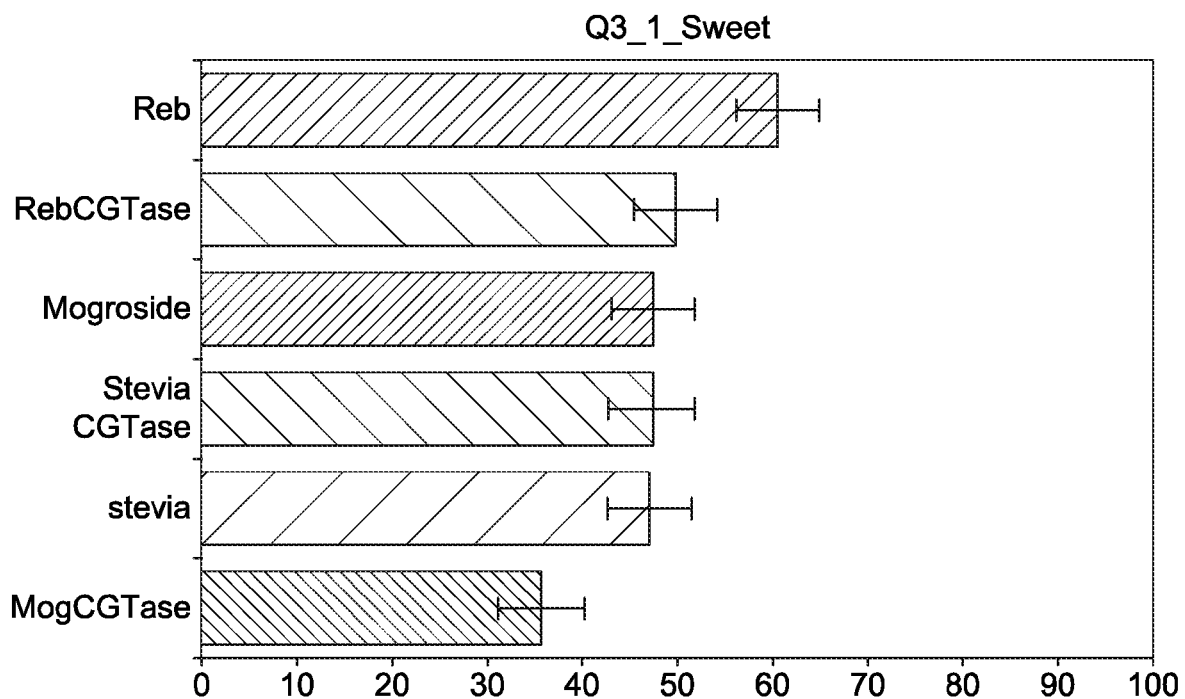
FIG. 1 is a bar chart showing the key attributes found to be significantly different between samples of Example 1 for a sweet taste (bars represent mean values, error bars extend+/−half LSD)
Figure 2:
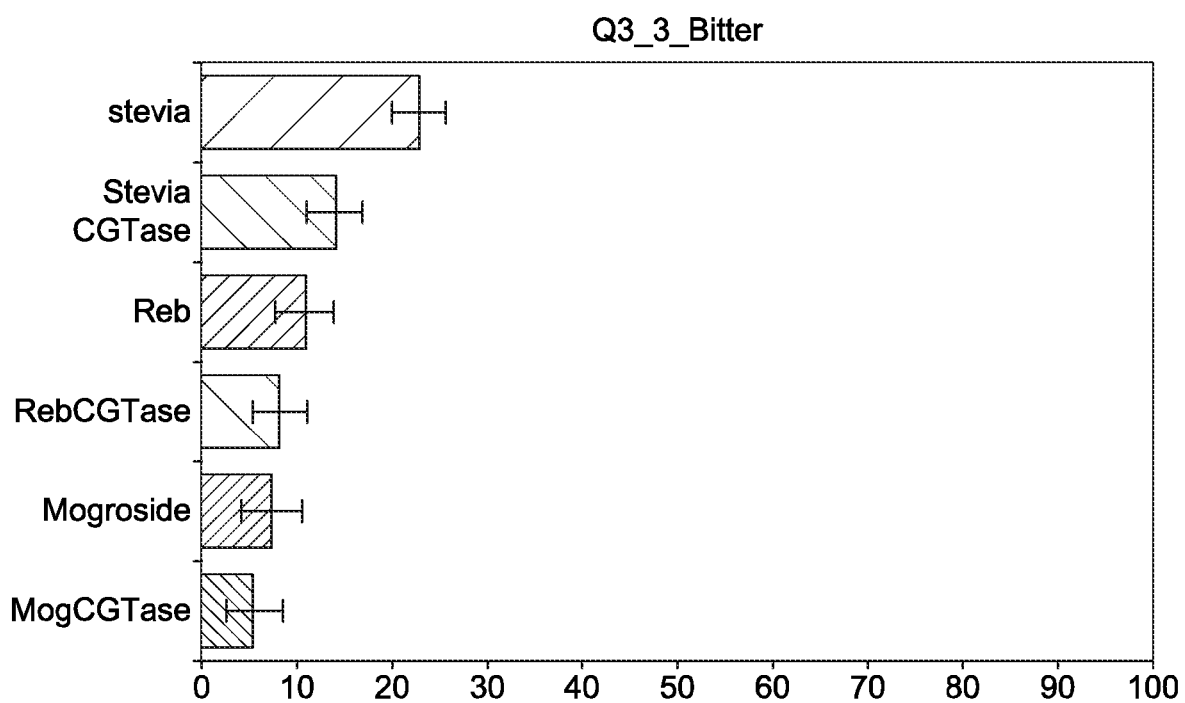
FIG. 2 is a bar chart showing the key attributes found to be significantly different between samples of Example 1 for a bitter taste (bars represent mean values, error bars extend+/−half LSD)

FIGS. 1 to 3 show the key attributes found to be significantly different between samples for sweet taste, bitter taste and liquorice flavour. Although the sucrose standards were not rated in a blinded manner, it is useful to compare the mean sweetness values samples to the sweetness values of the four sucrose standards. A dose-response curve for the sweetness of the sucrose standards was prepared and within the range of concentrations used, the relationship was linear and the linear regression equation was: Sweetness=15.5 (sucrose)−22.5 (R-square=0.99). Using this regression equation the sweetness values of the samples were converted to equivalent sucrose (ES) concentrations. This has been done from the mean sweetness rating. The values of ES and potency values are shown in Table 3 below.

TABLE 3

| | Sweet Taste Intensity | Concentration (g/L) | ES (%) | Potency |
|---|---|---|---|---|
| Steviol glycosides | 46.9 | 0.032 | 4.5 | 140 |
| Steviol glycosides CGTase | 47.1 | 0.032 | 4.5 | 140 |
| Rebaudioside A | 60.3 | 0.024 | 5.3 | 223 |
| Rebaudiosidea A CGTase | 49.6 | 0.024 | 4.7 | 194 |
| Mogroside V | 47.3 | 0.024 | 4.5 | 188 |
| Mogroside V CGTase | 35.6 | 0.024 | 3.7 | 56 |

The high intensity sweeteners prepared in water at either 0.032 or 0.024 g/L varied from providing the same sweetness as equivalent (on average) to between 3.7% and 5.3% sucrose, leading to potency values of between 140× and 223× sucrose.

EXAMPLE 2

Comparison of Enzymatic Modification of Steviol Glycosides and Rebaudioside a from *Stevia rebaudiana* and Mogroside V from *Siraitia grosvenorii*

The aim of this experiment was to assess the yield of enzymatic modification of steviol glycosides and rebaudioside A from *Stevia rebaudiana* and mogroside V from *Siraitia grosvenorii*.

Enzymatic Synthesis

Synthesis was carried out using maltodextrin, three different target sweeteners (steviol glycosides, rebaudioside A and mogroside V) and three different commercial cyclodextrin glycosyltransferases (CGTase) from *Paenibacillus macerans, Thermoanaerobacter* sp and *Geobacillus* sp.

An experimental design (DoE) (Factorial design and Central Composite Design (CCD) was also carried out to determine the best synthesis conditions so as to produce higher productivity.

Three CGTases from three different microorganisms were compared for the synthesis of new glycosylated steviol glycosides and mogroside V. One of the main problems with currently available commercial sweeteners is after-taste.

Table 4 shows the yield of the new products; the values are obtained from all CCD design optimization.

TABLE 4

| | % Yield | | |
|---|---|---|---|
| Enzymes/Subtract | Steviol glycosides | Rebaudioside A | Mogroside V |
| CGTase from *Paenibacillus macerans* | 21.8 | 10.0 | 53.2 |
| CGtase from *Thermoanaerobacter* sp | 30.0 | 58.3 | 88.6 |
| CGTase from *Geobacillus* sp | 31.1 | 57.0 | 46.1 |

Purification

After synthesis, samples for structural and sensory analysis were purified using Diaion® HP-20 resin to eliminate any free carbohydrates from the mixture. The resin and the corresponding eluents (ethanol/water) were food grade.

The objective of this step was to obtain a product free of oligosaccharides which could interfere in the sensory and structural analysis. After this purification, the purity of new compounds obtained after enzymatic synthesis were 90-95% w/w for all treatments.

Structural Analysis

Quantification was carried out using LC-DAD (C18 column). Structural characterization was carried out using MALDI-ToF to determine the number of monomers unit attached after enzymatic reaction.

Table 4 above outlines the relative quantification of the yield of each target sweetener with each CGTase. FIGS. 4A-C shows the different LC-DAD profiles for each treatment with the corresponding compound before and after the enzymatic synthesis.

According to FIGS. 4A-C, all treatments generated new compounds with shorter retention times. Since, the column used was a C18 (reverse phase), it seems that the new compounds found are more hydrophilic. In this case, hydrophilicity is generated by the addition of glucose units to the steviol glycosides and mogroside V.

According to FIG. 5A-C, Steviol glycosides and Rebaudioside A, structural characterization by mass spectrometry found up to 13 and 19 glucosyl residues attached to the steviol aglycone, whereas for Mogroside V, up to 20 glucosyl residues were found to be attached to the aglycone.

The forgoing embodiments are not intended to limit the scope of the protection afforded by the claims, but rather to describe examples of how the invention may be put into practice.

The invention claimed is:

1. A method for modifying a high intensity sweetener glycoside so as to reduce one or more off flavors, the method comprising:
   a) contacting the high intensity sweetener glycoside with a cyclodextrin glycosyltransferase (CGTase) in the presence of maltodextrin under conditions effective to result in:
      (i) at least a partial increase of glycoside chains of the high intensity sweetener glycoside; and/or
      (ii) at least a partial increase of the glycoside chains of a portion of the high intensity sweetener glycoside;

so as to form modified high intensity sweetener glycosides or mixture of partially modified high intensity sweetener glycosides, wherein the high intensity sweetener glycoside is a Mogroside.

2. The method of claim 1, wherein the Mogroside comprises Mogroside V.

3. The method of claim 2, wherein the CGTase is derived from a bacterium, wherein the bacterium is *Thermoanaerobacter*.

4. A method of sweetening foods, the method comprising incorporating the high intensity sweetener glycoside modified according to claim 1 in a foodstuff, a food supplement, or a calorie restricted meal replacement product as a low or reduced calorie sweetener.

5. The method as claimed in claim 4, wherein the low or reduced calorie sweetener is a sucrose replacer.

* * * * *